United States Patent [19]

Lillwitz et al.

[11] Patent Number: 4,721,808

[45] Date of Patent: Jan. 26, 1988

[54] PROCESS FOR PURIFICATION OF CRUDE P-HYDROXYMETHYLBENZOIC ACID

[75] Inventors: Lawrence D. Lillwitz, Glen Ellyn; Steven A. Cerefice, Naperville, both of Ill.

[73] Assignee: Amoco Corporation, Chicago, Ill.

[21] Appl. No.: 40,887

[22] Filed: Apr. 21, 1987

[51] Int. Cl.$^4$ ............................................. C07C 65/00
[52] U.S. Cl. ..................................................... 562/473
[58] Field of Search ......................................... 562/473

[56] References Cited

U.S. PATENT DOCUMENTS 4,448,987  5/1984  Lillwitz ............................... 562/473

FOREIGN PATENT DOCUMENTS 186905  3/1966  U.S.S.R. ............................... 562/473
910594  7/1982  U.S.S.R. ............................... 562/473

*Primary Examiner*—Paul J. Killos
*Attorney, Agent, or Firm*—William C. Clarke; Gunar J. Blumberg; William H. Magidson

[57] ABSTRACT

A crude p-hydroxymethylbenzoic acid compound containing 4-carboxybenzaldehyde is purified and decolorized by hydrogenation in the presence of a platinum on carbon catalyst. 4-carboxybenzaldehyde is hydrogenated to p-hydroxymethylbenzoic acid. Toluic acid is not a product of the hydrogenation process.

12 Claims, No Drawings

PROCESS FOR PURIFICATION OF CRUDE P-HYDROXYMETHYLBENZOIC ACID

FIELD OF THE INVENTION

This invention relates to a method for the elimination of color and of purifying hydroxymethyl aryl monocarboxylic acid compounds produced from arylene dicarboxylic acids in a catalyzed hydrogenation. More particularly, it relates to the elimination of color bodies in crude p-hydroxymethylbenzoic acid and to the selective reduction of 4-carboxybenzaldehyde in the presence of p-hydroxymethylbenzoic acid with a platinum catalyst to hydrogenate one aldehyde group to a hydroxymethyl group of the 4-carboxybenzaldehyde and yet is selective enough to prevent overreduction (hydrogenolysis) of the hydroxymethyl group of p-hydroxymethylbenzoic acid to toluic acid, and selective enough to prevent reduction of the carboxylic acid group of the 4-carboxybenzaldehyde.

BACKGROUND OF THE INVENTION p-Hydroxymethylbenzoic acid (pHMBA) is an important monomer for preparation of poly(p-methylenebenzoate). Poly(p-methylenebenzoate) is prepared from pHMBA by polymerization under polycondensation and melt polymerization conditions in the presence of a suitable catalyst.

Numerous methods are known for the preparation of p-hydroxymethylbenzoic acid. Among other methods, some of these are based on the saponification of a corresponding halogenmethyl compound, such as p-chloromethylbenzoic acid or the esters thereof or p-chloromethylbenzonitrile. For example, several methods for the synthesis of p-hydroxymethylbenzoic acid are taught in U.S. Pat. No. 4,130,719. The electrochemical reduction of terephthalic acid to p-hydroxymethylbenzoic acid is taught in commonly-assigned application Ser. No. 319,120, filed Nov. 9, 1981, now U.S. Pat. No. 4,381,229.

p-Hydroxymethylbenzoic acid must be free from byproducts when it is to be employed in polycondensation reactions, such as in the preparation of polyesters. However, most of the known processes for the preparation of p-hydroxymethylbenzoic acid do not yield the acid free from by-products. Thus, for example, during the saponification of highly pure p-chloromethylbenzoic acid in a faintly alkaline aqueous medium, up to 10% of dibenzylether-4,4'-dicarboxylic acid is always produced.

In other methods, as for example, in the electrochemical reduction of terephthalic acid to p-hydroxymethylbenzoic acid many competing reactions take place in the electrolysis cell. The resulting presence of 4-carboxybenzaldehyde (4-CBA), dihydroxymethylbenzene, toluic acid and other impurities which can act as color bodies render the resulting p-hydroxymethylbenzoic acid undesirable for use as a monomer for polymer applications without further expensive purification.

It is well-known that in the cathodic reduction of carboxylic acids that two types of products can result, either the corresponding aldehyde in a two-electron process or the hydroxymethyl compound in a four-electron process where the aldehyde is further reduced to the alcohol. (M. Baizer, Organic Electrochemistry, Deker, N.Y. (1973), 414) The alcohol can be further reduced to the methyl group.

4-Carboxybenzaldehyde and p-toluic acid, both of which occur in the electrochemical reduction of terephthalic acid to p-hydroxymethylbenzoic acid, and residual terephthalic acid act as polymer chain stoppers in polymerization of p-hydroxymethylbenzoic acid to poly(p-methylenebenzoate).

From mathematical calculations, a combined level of above 0.3 (wt) % of monocarboxylic acid impurities, i.e., 4-carboxybenzaldehyde and p-toluic acid, will limit molecular weight of the polymer chain and give a polymer with inferior mechanical properties and an inherent viscosity of less than about 0.6 deciliters/gram (dl/g) in a 60/40 phenol/tetrachloroethane solvent at 30° C. An inherent viscosity of at least 0.6 dl/g is suitable for preparation of molded parts having a tensile impact strength of at least 100 psi, according to ASTM D-1822, and for preparation of fibers and films of poly(p-methylenebenzoate).

Although residual terephthalic acid impurities in p-hydroxymethylbenzoic acid create a stoichiometric imbalance of hydroxyl and carboxylic acid units such that the resultant polymer has a predominance of carboxylic acid end groups, terephthalic acid can be incorporated into any location of the polymer chain with consequent limited weight development. As a result, higher levels of residual terephthalic acid impurity can be tolerated than levels of 4-carboxybenzaldehyde and p-toluic acid.

4-Carboxybenzaldehyde is a particularly undesirable impurity because it acts as a chain-stopper during polyesterification and can be present in significant quantities, in a ratio of about 2:1, to p-toluic acid, as taught in U.S. Pat. No. 3,850,983. Although 4-carboxybenzaldehyde is difficult to remove by physical means, it can be hydrogenated to toluic acid and other derivatives, but toluic acid also acts as a chain-stopper during polyesterification. Toluic acid can be efficiently removed by cooling and crystallizing crude p-hydroxymethylbenzoic containing it. 4-Carboxybenzaldehyde also can be hydrogenated to the hydroxymethyl compound, i.e., p-hydroxymethylbenzoic acid, in an electrochemical process as is taught by Baizer, mentioned above, but hydrogenation of crude terephthalic acid in an electrochemical process results in increased quantities of 4-carboxybenzaldehyde despite the concurrent hydrogenation of 4-carboxybenzaldehyde to p-hydroxymethylbenzoic acid.

Catalytic methods of hydrogenating 4-carboxybenzaldehyde typically result in the production of toluic acid. For example, in the purification of terephthalic acid containing 4-carboxybenzaldehyde, by catalytic hydrogenation, U.S. Pat. No. 4,260,817 teaches that hydrogenation of terephthalic acid using a bimetallic catalyst of palladium and platinum converts 4-carboxybenzaldehyde to p-toluic acid.

The presence of impurities which can act as color bodies is also highly undesirable. Color may appear in the newly-manufactured p-hydroxymethylbenzoic acid or can develop on standing or exposure to elevated temperatures or actinic light. Such color-forming impurities are occluded in the acid crystals and carry over into resins made from the acids, reducing or obliterating the market value of the end product. In uses which require less attention to color, the fact that the product is white or near white will still render the product more desirable. The process of this invention is useful in reducing the color of the acid produced thereby and consequently the color of the final resin.

A batch or continuous process has now been found for the hydrogenation of 4-carboxybenzaldehyde in the presence of p-hydroxymethylbenzoic acid as the ammonium salt prepared by electrochemical reduction of terephthalic acid wherein one carboxylic acid group is hydrogenated to a hydroxymethyl group using a platinum catalyst and yet is selective enough to prevent hydrogenolysis of the hydroxymethyl group of the p-hydroxymethylbenzoic acid to the methyl group and reduction of the second carboxylic acid to a hydroxymethyl group or to a methyl group. Color bodies are also reduced. More specifically, a process has been found for the purification of the ammonium salt of p-hydroxymethylbenzoic acid by the reduction of 4-carboxybenzaldehyde and color bodies in the presence of a platinum catalyst under relatively mild conditions wherein conversion of the salt of p-hydroxymethylbenzoic acid is negligible and selectivity of 4-CBA to p-hydroxymethylbenzoic acid is within the range of from about 80% to 90%. Yields are accordingly within the range of about 90 (wt) % of 4-carboxybenzaldehyde present. Color is reduced from a Gardner 2-3 to less than a Gardner 1.

Unexpectedly, it has been found that a platinum catalyst has catalytic activity in aqueous solvent to selectively hydrogenate an ammonium or alkali metal or alkaline earth metal salt of 4-carboxybenzaldehyde to the equivalent salt of p-hydroxymethylbenzoic acid in yields of 90 (wt) % or better. Only the aldehyde group is reduced to the hydroxymethyl group.

Unexpectedly, it has been found that color bodies in the crude acid are eliminated by hydrogenation of 4-carboxybenzaldehyde in the crude acid using a platinum on carbon catalyst to obtain a water-white product suitable for resin production.

Color level of the purified salt of p-hydroxymethylbenzoic acid in batch or continuous process can be controlled effectively by modulating the hydrogen concentration in the impure solution while it is undergoing hydrogenation, in the method of U.S. Pat. No. 4,626,598, which is incorporated by reference.

Accordingly, it is an object of this invention to purify p-hydroxymethylbenzoic acid containing 4-carboxybenzaldehyde by hydrogenating 4-carboxybenzaldehyde to p-hydroxymethylbenzoic acid without increasing the level of p-toluic acid present.

It is a further object of this invention to hydrogenate 4-carboxybenzaldehyde to p-hydroxymethylbenzoic acid, in the presence of p-hydroxymethylbenzoic acid, wherein over-hydrogenation is controlled, as over-hydrogenation can produce not only p-toluic acid, but also a number of hydrogenated aromatic products including cyclohexane and several hydrogenated aromatic acids such as 1,4 dicarboxylic acid.

It is a further object of this invention to prepare p-hydroxymethylbenzoic acid in a highly purified state wherein color is less than Gardner 1.

It is a further object of this invention to prepare p-hydroxymethylbenzoic acid in a highly-purified state for polymerization to poly(p-methylenebenzoate), the said poly(p-methylenebenzoate) having an inherent viscosity of greater than 0.6 dl/g in a 60/40 phenol/tetrachloroethane solvent at 30° C.

SUMMARY OF THE INVENTION

A process is disclosed for purification of a salt of p-hydroxymethylbenzoic acid, in aqueous solution containing 4-carboxybenzaldehyde wherein said 4-carboxybenzaldehyde is catalytically selectively hydrogenated to p-hydroxymethylbenzoic acid in absence of over-hydrogenation of said 4-carboxybenzaldehyde to p-toluic acid and of said salt of p-hydroxymethylbenzoic acid, color bodies are greatly eliminated, and wherein catalyst for said process is platinum on carbon.

DETAILS OF THE INVENTION

In the preparation of p-hydroxymethylbenzoic acid by electrochemical reduction of the terephthalic acid, the catholyte can comprise a weakly basic solvent such as water with a soluble ammonium salt and ammonia with terephthalic acid. The product is a crude ammonium salt of p-hydroxymethylbenzoic acid with a number of by-products, the ammonium salt of 4-carboxybenzaldehyde, the ammonium salt of toluic acid, and the ammonium salt of terephthalic acid. The crude product is partially purified by using the difference in water solubility of the terephthalic acid salt and the p-hydroxymethylbenzoic acid salt. The crude product in aqueous solution is filtered hot, within a temperature range of from about 75° C. to about 150° C. to remove the terephthalic acid salt. The mother liquor is then cooled to a temperature below 40° C., preferably below 25° C. The partially purified salt of p-hydroxymethylbenzoic acid in aqueous solution is thereupon further purified by hydrogenation of the 4-carboxybenzaldehyde ammonium salt to the ammonium salt of p-hydroxymethylbenzoic acid.

Catalytic hydrogenation of 4-carboxybenzaldehyde in aqueous solution using a platinum on carbon catalyst surprisingly has been found to be highly selective in the products obtained. Thus in accordance with the invention, it has been found possible to reduce the presence of 4-carboxybenzaldehyde from approximately 17 (wt) % of the cell product to less than 0.08(wt) % of the cell product by selectively hydrogenating the 4-carboxybenzaldehyde to p-hydroxymethylbenzoic acid. Additional toluic acid is not a product. Color bodies are reduced or eliminated. Gardner color of the purified p-hydroxymethylbenzoic acid is less than 1.

It is essential that the process is carried out in the presence of a solvent in which both the starting materials and the end products are sufficiently soluble. Solvents which can be used are polar solvents such as water and alcohols such as lower aliphatic monohydric alcohols, preferably containing from 1 to 8 carbon atoms, for example, methanol, cycloaliphatic alcohols such as cyclohexanol, and polyhydric alcohols such as butanediol or glycerol. Solvents other than water or alcohols such as lower aliphatic monohydric and polyhydric alcohols are unsuitable because either starting materials or end products are not sufficiently soluble.

It is essential that the solution be basic, of a pH greater than 7, to maintain the solubility of starting materials and end products. Ammonium compounds or soluble compounds of alkali metals or alkaline earth metals can be used to maintain the basic condition. Ammonia, or oxides of alkali metals or alkaline earth metals are preferred to maintain the basic condition. Ammonia is most preferred because crude product from electrochemical reduction of terephthalic acid is the ammonium salt.

The use of catalysts other than platinum on carbon, or platinum oxide, $PtO_2$, has been found to be of little value in hydrogenation of 4-carboxybenzaldehyde to p-hydroxymethylbenzoic acid since toluic acid is produced in quantity, an undesirable impurity in product for polymerization to poly(p-methylenebenzoate). In one example, toluic acid content of p-hydroxymethylbenzoic acid electrochemical cell product increased from 3800 parts per million (ppm) to 8700 ppm after hydrogenation using a palladium on carbon catalyst. The use of platinum on carbon or platinum oxide as catalyst is accordingly essential.

The catalyst is preferably used in a quantity of from 0.1 (wt) % to 30 (wt) % of the crude cell product from the electrochemical reduction of terephthalic acid, preferably from 2 (wt) % to 20 (wt) %, more preferably of from 3 (wt) % to 10 (wt) %.

In general, the hydrogen pressure employed during the process is preferably from about 500 psig to about 1500 psig, more preferably from about 800 psig to about 1200 psig. It is essential that the hydrogenation reaction temperature is less than about 75° C., preferably less than about 50° C. At temperatures above 75° C., excessive amounts of toluic acid are produced.

Separation of the p-hydroxymethylbenzoic acid from the crude p-hydroxymethylbenzoic acid compound can be obtained by cooling the solution to a temperature of less than 40° C. to effect crystallization. The catalyst can be recovered by filtration of the mother liquid from the crystallization.

The catalyst, platinum on carbon, can be a commercially available catalyst containing 5 (wt) % platinum on carbon. A typical catalyst useful in this invented process is Engelhard No. 50294, platinum on carbon, wherein the carbon is derived from coconut charcoal, and platinum content is 5 (wt) %.

It is postulated that the selective reduction of the carbonyl group to the hydroxymethyl group can even be carried out under hydrogen pressure slightly greater than atmospheric but increased product production is obtained with higher hydrogen pressures such as at 1000 psi.

Since solubilities of p-hydroxymethylbenzoic acid and impurities in solvents depend upon the temperature at which the reaction takes place, increased product production is obtained by increased temperature and pressure. As shown in the following table, solubilities of the respective compounds increase significantly with increase in temperature.

| Solubilities of pHMBA and Impurities in Water | | |
|---|---|---|
| | Solubility (g/100 ml $H_2O$) | |
| Compound | at 20° C. | at 100° C. |
| pHMBA | ~0.5 | ~10.0 |
| p-Toluic Acid | 0.02 | 0.22 |
| 4-CBA | <0.005 | ~0.25 |
| Terephthalic Acid | <0.005 | 0.03 |

Accordingly, reactor pressure conditions primarily depend upon the temperature at which the purification process is carried out. Inasmuch as the temperatures at which practical amounts of the impure p-hydroxymethylbenzoic acid may be dissolved are substantially above the normal boiling point of the solvent, the process pressures are necessarily above atmospheric pressure to maintain the solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 200 to about 1500 pounds per square inch gauge (psig), and usually is in the range of about 800 psig to about 1,200 psig.

The hydrogenation reactor can be operated in several models. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the p-hydroxymethylbenzoic acid solution present is the hydrogen partial pressure in the reactor vapor space. Alternatively, if hydrogen is fed in admixture with an inert gas such as nitrogen, the difference between the actual reactor pressure and the vapor pressure of the pHMBA solution present is the combined partial pressure of hydrogen and the inert gas admixed therewith. In this case the hydrogen partial pressure can be calculated from the known relative amounts of hydrogen and inert gas present in the admixture.

In yet another operating mode the reactor can be filled with the pHMBA solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode wherein reactor pressure is in the range of from 200 to about 1500 psig, where process control is effected by adjusting the hydrogen partial pressure, the hydrogen partial pressure in the reactor can be as low as 10 psig to about 200 psig, depending upon the service pressure rating of the reactor, the degree of combination of the impure pHMBA, the activity and age of the particular catalyst employed, and like processing considerations. A higher hydrogen partial pressure of from 800 to 1200 psig, however, is preferred.

In the operating mode where process control is effected by adjusting directly the hydrogen concentration in the feed solution, the latter usually is less than saturated with respect to hydrogen and the reactor itself is hydraulically full. Thus an adjustment of the hydrogen flow rate to the reactor will result in the desired control of hydrogen concentration in the solution.

The process can be operated either by batch or continuous method. A continuous process is preferable. The presence of carbon monoxide in a 4-CBA hydrogenation reactor is recognized by the prior art to be a problem (see, for example, U.S. Pat. No. 4,201,872 to Kimura) because carbon monoxide is known to inhibit the activity of hydrogenation catalysts. The present process in a continuous process can avoid this problem, however, by maintaining conditions favorable to carbon monoxide generation away from the Pt/C catalyst layer, that is, by sweeping the produced carbon monoxide from the catalyst bed by an effluent stream.

In a continuous method, space velocity (lbs pHMBA solution/lb catalyst/hr) of the aqueous crude pHMBA solution through the catalyst bed is about 5 hours⁻¹ to about 25 hours⁻¹, preferably about 10 hours⁻¹ to about 15 hours⁻¹.

The catalyst carrier is active carbon, usually that derived from coconut charcoal in the form of granules having a surface area of at least about 600 m²/g (N₂; BET Method), preferably about 800 m²/g to about 1500 m²/g. However, other porous carbonaceous supports or substrates can be used as long as the surface area requirements can be met. In addition to coconut charcoal, activated carbon derived from other plant or from animal sources can be utilized, such as bone char.

Catalyst metal loading on the carrier for platinum can be in the range of from about 0.1 weight percent to about 10 weight percent, based on the total weight of the catalyst, i.e., metal plus active carbon carrier, and calculated as elemental metal. Preferably the platinum metal loading is about 5 weight percent. Such catalysts are commercially available.

A suitable Pt/C catalyst can be obtained, for example, from Engelhard Corporation, Newark, N.J. under the designation "Platinum on Activated Carbon Granules (Carbon Code CG-5)." This Pt/C catalyst has a BET;N₂ surface area of about 1,000 m²/gram and a particle size of 4×8 mesh, U.S. Sieve Series. Other suitable Pt/C catalysts of similar size and surface area are available from ASAR, Johnson Matthey Inc., Seabrook, N.H., under the designation "Platinum 5% on Steam Activated Coconut Shell Carbon, Anhydrous."

For conversion of 4-CBA to pHMBA, the stoichiometric hydrogen requirement is one mole of hydrogen for each mole of 4-CBA so converted. Preferably the amount of hydrogen supplied to the reaction is about two times that stoichiometrically required for the reaction.

Accordingly, the instant invented process comprises a process for purification and decolorization of a crude p-hydroxymethylbenzoic acid compound containing 4-carboxybenzaldehyde and color bodies by hydrogenation to prepare purified p-hydroxymethylbenzoic acid which process comprises: (a) preparing a basic solution of said crude p-hydroxymethylbenzoic acid compound in a polar solvent wherein pH of said solution is greater than 7 to solubilize said compound; (b) passing hydrogen through said solution to hydrogenate said crude p-hydroxymethylbenzoic acid compound containing 4-carboxybenzaldehyde and color bodies to hydrogenate said 4-carboxybenzaldehyde and said color bodies, in the presence of a platinum catalyst at a temperature less than 75° C., said 4-carboxybenzaldehyde being hydrogenated to a p-hydroxymethylbenzoic acid compound; (c) separating p-hydroxymethylbenzoic acid compound from said crude p-hydroxymethylbenzoic acid compound and from said 4-carboxybenzaldehyde in said solution by cooling said solution to effect crystallation, wherein said purified p-hydroxymethylbenzoic acid is characterized by a color of less than Gardner 1. The catalyst of the invented process is platinum on a substrate carrier of active carbon in the form of granules having a surface area of at least about 600 m²/g (N₂; BET Method) and catalyst platinum loading is from about 0.1 weight percent to about 10 weight percent of metal plus active carbon carrier, calculated as elemental metal.

Preferably, the platinum loading of the catalyst is about 5 weight percent of metal plus active carbon carrier, calculated as elemental metal. Most preferably, the process is a continuous process, the polar solvent is water, the catalyst is 5% by weight platinum metal upon an active carbon derived from coconut charcoal in the form of granules having a surface area from about 800 m²/g to about 1500 m²/g (N₂; BET Method), hydrogen pressure is within the range of from about 800 psig to about 1200 psig, temperature is less than 50° C., and space velocity is within the range of from about 5 hours⁻¹ to about 25 hours⁻¹. Alternatively, the catalyst can be platinum oxide, PtO₂.

Without limiting the invention, the present invention is illustrated further by the following examples.

EXAMPLE I

The ability of Pt/C catalyst to convert 4-CBA to pHMBA without increasing the level of toluic acid was tested.

Two liters of crude electrochemical cell product, composition shown in Table I, and 5.0 g of 5% Pt/C catalyst (Engelhard-Lot 26,075-S.O. 10740) was charged to a one-gallon autoclave equipped with a glass liner insert. pH was basic enough to obtain complete solution of the crude electrochemical cell product. The reactor was pressurized to 1000 psi hydrogen at 22°-23° C. and held at that temperature for two hours and twenty minutes. The solution was filtered and analyzed by liquid chromatography (LC). The 4-CBA level was reduced from 2.5% to 0.25%. This solution was further treated at 50° C. for two hours and forty minutes using the same 5% Pt/C catalyst from the first treatment. The reaction solution was filtered and analyzed by liquid chromatography (LC) to give 0.05% 4-CBA as shown in the following:

TABLE I

|  | mg/ml | | | |
|---|---|---|---|---|
|  | pHMBA | TA | 4-CBA | Toluic Acid |
| Crude cell product | 94.7 | 6.0 | 2.56 | 0.12 |
| First hydrogenation | 93.8 | 6.0 | 0.26 | 0.12 |
| Second hydrogenation | 94.0 | 6.1 | 0.05 | 0.10 |

EXAMPLE II

To the same type autoclave as in Example I 1400 ml of a similar crude cell product spiked with 30 g of 4-CBA to give the composition shown in Table II and 5.0 g of 5% Pt/C (Engelhard No. 50294) was charged. pH was basic to obtain complete solubility of the crude cell product. The reactor was pressured to 1000 psi at a temperature of 21°-24° C. and reacted for 6 hours. The hydrogen pressure fell from 1000 psi to 920 psi. After the reaction solution was filtered it was analyzed by liquid chromatography (LC) to show the following:

TABLE II

|  | mg/ml | | | |
|---|---|---|---|---|
|  | pHMBA | TA | 4-CBA | Toluic Acid |
| Before hydrogenation | 59.6 | 18.8 | 16.6 | 0.32 |
| After hydrogenation | 74.7 | 19.0 | 0.07 | 0.32 |

EXAMPLE III

Using conditions identical to those in Example II (Pt/C hydrogenation) the results with Pd/C show a significant increase in the toluic acid concentration.

The same autoclave as in Example II was charged with 300 ml of crude cell product spiked with 4.0 g of 4-CBA to give the composition shown in Table III and 0.67 g of 5% Pd/C. The reactor was pressured to 1000 psi at a temperature of 21°–22° C. and reacted for eight hours. pH was basic as in Example II. The hydrogen pressure fell from 1000 psi to 970 psi. The reaction solution was filtered and analyzed by liquid chromatography (LC) to give the following:

TABLE III

| | mg/ml | | | |
|---|---|---|---|---|
| | pHMBA | TA | 4-CBA | Toluic Acid |
| Before hydrogenation | 61.9 | 19.0 | 11.4 | 0.38 |
| After hydrogenation | 73.8 | 20.5 | 0.04 | 0.87 |

EXAMPLE IV

The ability of platinum as platinum oxide catalyst to convert 4-CBA to pHMBA was tested.

A 300 ml capacity rocking autoclave bomb was charged with 10.0 g (66 mmol) of 4-CBA (Aldrich, 97.3%), 100 ml of water containing 2.72 g (68 mmol) of NaOH, and 0.50 g (2.2 mmol) of $PtO_2$. pH was basic as in Example II. The mixture was pressured to 600 psi with hydrogen and shaken at 22° C. for 4 hours. After 1 hour the pressure had dropped 130±10 psi (theory for 100% conversion, 126 psi). The catalyst was filtered and washed with water. The aqueous filtrate was concentrated to 40 ml and neutralized with concentrated HCl. A yield of 9.78 g (96.5%) of product was obtained after filtering, washing with water, and drying. Analysis (silylation gc): 95.8% pHBMA, 2.91% TA, 1.10% p-toluic acid, 0.17% benzoic acid, and less than 0.10% 4-CBA.

EXAMPLE V

The ability of platinum on carbon catalyst to reduce or substantially eliminate color bodies in crude p-hydroxymethylbenzoic acid prepared by electrochemical reduction of terephthalic acid was tested.

Samples of the crude electrochemical cell product of Example I, of the composition shown in Table I, were measured as to color before and after hydrogenation by the procedure of Example I.

Before hydrogenation, color of the crude electrochemical cell product of Example I was Gardner 2-3. After hydrogenation, color of the crude cell product was less than Gardner 1.

Samples of the crude electrochemical cell product before hydrogenation were stored in glass containers and held at room temperature, with exposure to actinic radiation from daylight and artificial light. After approximately one year of such exposure, the crude sample without hydrogenation had turned a dark brown.

Samples of the same crude electrochemical cell product, wherein color was less than Gardner 1, after one year under the same storage conditions as the unhydrogenated samples, retained a color of less than Gardner 1.

What is claimed is:

1. A process for purification and decolorization of a crude p-hydroxymethylbenzoic acid compound containing 4-carboxybenzaldehyde and color bodies by hydrogenation to prepare purified p-hydroxymethylbenzoic acid which process comprises:
   (a) preparing a basic solution of said crude p-hydroxymethylbenzoic acid compound in a polar solvent wherein pH of said solution is greater than 7 to solubilize said compound;
   (b) passing hydrogen through said solution to hydrogenate said crude p-hydroxymethylbenzoic acid compound containing 4-carboxybenzaldehyde and color bodies to hydrogenate said 4-carboxybenzaldehyde and said color bodies, in the presence of a platinum catalyst, at a temperature less than 75° C., said 4-carboxybenzaldehyde being hydrogenated to a p-hydroxymethylbenzoic acid compound, wherein said solution after hydrogenation is characterized by a color of less than Gardner 1; and
   (c) separating p-hydroxymethylbenzoic acid compound from said 4-carboxybenzaldehyde in said solution by neutralizing and cooling said solution to effect crystallization.

2. The process of claim 1 wherein said polar solvent is selected from the group consisting of water and lower aliphatic monohydric alcohols of 1 to 8 carbon atoms.

3. The process of claim 1 wherein said pH is maintained by an excess of a compound selected from the group consisting of an ammonium compound, soluble compounds of alkali metals, and soluble compounds of alkaline earth metals.

4. The process of claim 1 wherein said platinum catalyst is present in a quantity of from about 0.1 (wt. %) to about 30 (wt.) % of said crude p-hydroxymethylbenzoic acid compound.

5. The process of claim 1 wherein reactor pressure is within the range of from about 200 psig to about 1500 psig.

6. The process of claim 5 wherein hydrogen pressure during said hydrogenation is within the range of from about 800 to about 1200 psig.

7. The process of claim 1 wherein said catalyst is platinum on a substrate carrier of active carbon in the form of granules having a surface area of at least about 600 $m^2/g$ ($N_2$; BET Method) and catalyst platinum loading is from about 0.1 weight percent to about 10 weight percent of metal plus active carbon carrier, calculated as elemental.

8. The process of claim 7 wherein said surface area of said active carbon of said substrate carrier is from about 800 $m^2/g$ to about 1500 $m^2/g$ ($N_2$; BET Method).

9. The process of claim 1 wherein said platinum loading is about 5 weight percent of metal plus active carbon carrier, calculated as elemental metal.

10. The process of claim 1 wherein said process is a continuous process, said polar solvent is water, said catalyst is 5% by weight platinum metal upon an active carbon derived from coconut charcoal in the form of granules having a surface area from about 800 $m^2/g$ to about 1,500 $m^2/g$ ($N_2$; BET Methods), hydrogen pressure is within the range of from about 800 psig to about 1200 psig, temperature is within the range of from about 20° C. to about 25° C., and space velocity is within the range of from about 5 $hours^{-1}$ to about 25 $hours^{-1}$.

11. The process of claim 1 wherein said catalyst is platinum oxide, $PtO_2$.

12. The process of claim 1 wherein said process is a batch process.

* * * * *